United States Patent
Nickerson et al.

(10) Patent No.: US 6,423,120 B1
(45) Date of Patent: Jul. 23, 2002

(54) SAMPLE INTRODUCTION SYSTEMS AND METHODS

(75) Inventors: Mark A. Nickerson, Landenberg; Clayton E. Law, Malerin; Rich White, Glen Mills, all of PA (US)

(73) Assignee: Agilent Technologies, Inc., Palo Alto, CA (US)

( * ) Notice: Subject to any disclaimer, the term of this patent is extended or adjusted under 35 U.S.C. 154(b) by 0 days.

(21) Appl. No.: 09/617,215

(22) Filed: Jul. 17, 2000

(51) Int. Cl.[7] ............................................... B01D 15/08
(52) U.S. Cl. .................... 95/87; 96/105; 210/198.2; 210/656; 73/23.41; 427/126.3
(58) Field of Search .................... 95/82, 87; 96/101, 96/105; 210/198.2, 656; 73/23.22, 23.35, 23.41; 422/89; 427/126.3

(56) References Cited

U.S. PATENT DOCUMENTS

| | | | |
|---|---|---|---|
| 3,558,959 A | 1/1971 | Ziemendorf | 313/130 |
| 4,471,647 A | 9/1984 | Jerman et al. | 73/23 |
| 4,581,204 A | 4/1986 | Voit | 422/90 |
| 4,726,822 A * | 2/1988 | Cates et al. | 210/198.2 |
| 5,114,439 A * | 5/1992 | Yost et al. | 95/87 |
| 5,135,549 A | 8/1992 | Phillips et al. | |
| 5,402,668 A * | 4/1995 | Murakami et al. | 95/87 |
| 5,756,991 A | 5/1998 | Risinger et al. | 250/252.1 |
| 5,779,765 A * | 7/1998 | Grob et al. | 95/87 |
| 5,782,964 A * | 7/1998 | Mustacich | 96/102 |
| 5,801,297 A | 9/1998 | Mifsud et al. | 73/23.34 |
| 5,876,635 A | 3/1999 | Jeong et al. | 252/520.1 |
| 6,209,386 B1 * | 4/2001 | Mustacich et al. | 95/87 |

* cited by examiner

Primary Examiner—David A. Simmons
Assistant Examiner—Frank M. Lawrence (57) ABSTRACT

A preferred sample introduction apparatus includes a wall that defines a channel, with the channel being configured to receive a sample and being adapted to engage in fluid communication with the separation column of a chromatographic apparatus. Preferably, a coating of semi-conductive material is arranged adjacent to at least a portion of the wall. Additionally, a heater controller is provided which electromagnetically communicates with the coating. So configured, the coating, in response to receiving energy from the heater controller, increases in temperature, thereby increasing a temperature of the sample.

53 Claims, 5 Drawing Sheets

SAMPLE INTRODUCTION SYSTEMS AND METHODS

BACKGROUND OF THE INVENTION

1. Field of the Invention

The present invention generally relates to chromatographic analysis and, in particular, to sample introduction systems, which are adapted for receiving a sample to be analyzed and for delivering the sample to a separation column of a gas chromatograph, and related methods.

2. Description of the Related Art

Gas chromatography is a method for analyzing a sample, which may include one or more analytes, to qualitatively determine the identity of the analytes as well as to quantitatively determine the concentration of each of the analytes. Gas chromatography typically involves a series of steps, including: sample collection, sample preparation, sample introduction into a chromatographic or separation column, chromatographic separation of the sample into individual analytes, detection of those analytes, and data acquisition and reduction.

In order to conduct gas chromatography, a gas chromatograph is utilized which typically incorporates: a sample introduction system configured to receive the sample and to mix the sample with an inert fluid; a separation column through which the various analytes of the sample traverse, and; a detector for measuring the presence of each of the analytes. The design of such a gas chromatograph is based on the premise that the combination of analytes making up the sample will separate as they traverse the separation column at different rates and, subsequently, exit the column at different retention times.

Due to the great variety of separation column configurations and the diversity of samples that can be analyzed, several sample introduction systems are known; however, no single system can best satisfy all analytical requirements. As a general principle, however, a sample introduction system is adapted to provide accurate, reproducible, and predictable introduction of a sample into the separation column of a gas chromatograph. Typically, a sample introduction system includes a sample inlet into which a quantity of sample in liquid form is injected, such as by using a syringe. After injection, the sample then can be prepared, such as by heating, for delivery to the separation column of the gas chromatograph. Additionally, there are other known sample introduction systems that are adapted for introducing samples into a separation column when syringe injection is inappropriate, such as gas or liquid sampling valves, headspace autosamplers, thermal desorbers, purge and trap samplers, and pyrolyzers, for example.

Heretofore, useful techniques for introducing a sample into a chromatographic system have incorporated the use of a heating element for heating the sample, which oftentimes enters the sample introduction system in a liquid phase, so that a gaseous phase of the sample is introduced into the separation column. Typically, sample introduction systems facilitating such a technique have incorporated a sample inlet that is heated with a cartridge heater. Such an inlet heater commonly is formed of a block of material, such as aluminum or stainless steel, for instance, in which the cartridge heater and a temperature sensor is installed and into which the sample introduction column extends. Thus, when heating of the sample is desired, voltage is applied to the cartridge heater installed within the aluminum or stainless steel block, thereby heating the block, with the heat being transferred through the sample introduction column and to the sample predominately by conduction. Although these prior art systems have met with considerable success, they tend to be somewhat inefficient, suffer from slow transient performance, and, oftentimes, require the incorporation of large power supplies.

Therefore, there exists a need for improved systems and methods which address these and other shortcomings of the prior art.

SUMMARY OF THE INVENTION

Briefly described, the present invention relates to sample introduction systems, which are adapted for receiving a sample to be analyzed and for delivering the sample to a separation column of a gas chromatograph, and related methods. In a preferred embodiment, a chromatographic analytical instrument system for analyzing a sample incorporates a separation column adapted to receive a mixture of a carrier gas and at least a portion of a sample, and a sample introduction apparatus. Preferably, the sample introduction apparatus includes a wall defining a channel, a coating and a heater controller, with the channel being configured to receive the sample and being adapted to engage in fluid communication with the separation column. The coating preferably is formed at least partially of a semi-conductive material and is arranged adjacent to at least a portion of the wall, and the heater controller electro-magnetically communicates with the coating. So configured, an increase in the temperature of the coating is achieved after the coating receives electro-magnetic energy from the heater controller, thereby allowing the temperature of the sample to increase within the channel.

In accordance with another aspect of the present invention, a preferred embodiment of the sample introduction apparatus includes a wall which defines a channel, with the channel being configured to receive the sample and being adapted to engage in fluid communication with the separation column of the chromatographic apparatus. Preferably, a coating of semi-conductive material is arranged adjacent to at least a portion of the wall. Additionally, a heater controller provides electrical energy to the coating. The electrical energy generates an electric current in the resistive coating and the coating's electrical resistive properties convert the current flow into heat, that conducts at least a portion of the energy to the sample so that sample temperature increases within the channel of the sample introduction apparatus.

In accordance with another aspect of the present invention, an embodiment of the sample introduction apparatus includes a wall which defines a channel, with the channel being configured to receive the sample and being adapted to engage in fluid communication with the separation column of the chromatographic apparatus. Preferably, a coating of semi-conductive material is arranged adjacent to at least a portion of the wall. Additionally, means for heating the coating is provided. So configured, the coating, in response to the means for heating, conducts heat to the sample so that a temperature of the sample increases within the channel of the sample introduction apparatus.

In accordance with another aspect of the present invention, a method for providing a sample to a chromatographic apparatus comprises the steps of: providing a channel configured to receive the sample, the channel being adapted to engage in fluid communication with the separation column of the chromatographic apparatus, the channel having a coating of semi-conductive material arranged adjacent to at least a portion thereof; heating the coating so that a temperature of the sample increases within the channel, and; providing the sample to the separation column of the chromatographic apparatus.

Other objects, features, and advantages of the present invention will become apparent to one with skill in the art upon examination of the following drawings and detailed description. It is intended that all such objects, features, and advantages be included herein within the scope of the present invention, as defined in the appended claims.

BRIEF DESCRIPTION OF THE SEVERAL VIEWS OF THE DRAWINGS

The present invention, as defined in the claims, can be better understood with reference to the following drawings. The drawings are not necessarily to scale, emphasis instead being placed on clearly illustrating the principles of the present invention.

DETAILED DESCRIPTION OF A PREFERRED EMBODIMENT

Figure 1:
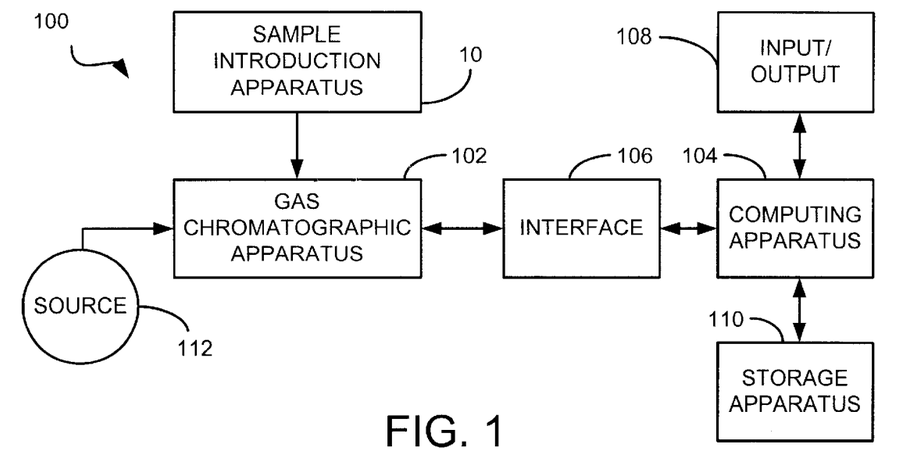
FIG. 1 is a schematic diagram of a preferred embodiment of the present invention.

Reference will now be made in detail to the description of the invention as illustrated in the drawings with like numerals indicating like parts throughout the several views. As shown in FIG. 1, a preferred embodiment of the analytical instrument system 100 of the present invention includes a sample introduction apparatus 10, a chromatographic apparatus 102, a computing apparatus 104, an interface 106 for interfacing chromatographic apparatus 102 and computing apparatus 104, an input/output 108, and a storage apparatus 110. A source of carrier gas 112, such as hydrogen, nitrogen, or helium, for example, depending upon the particular chromatographic separation to be performed, also is provided.

Figure 2:
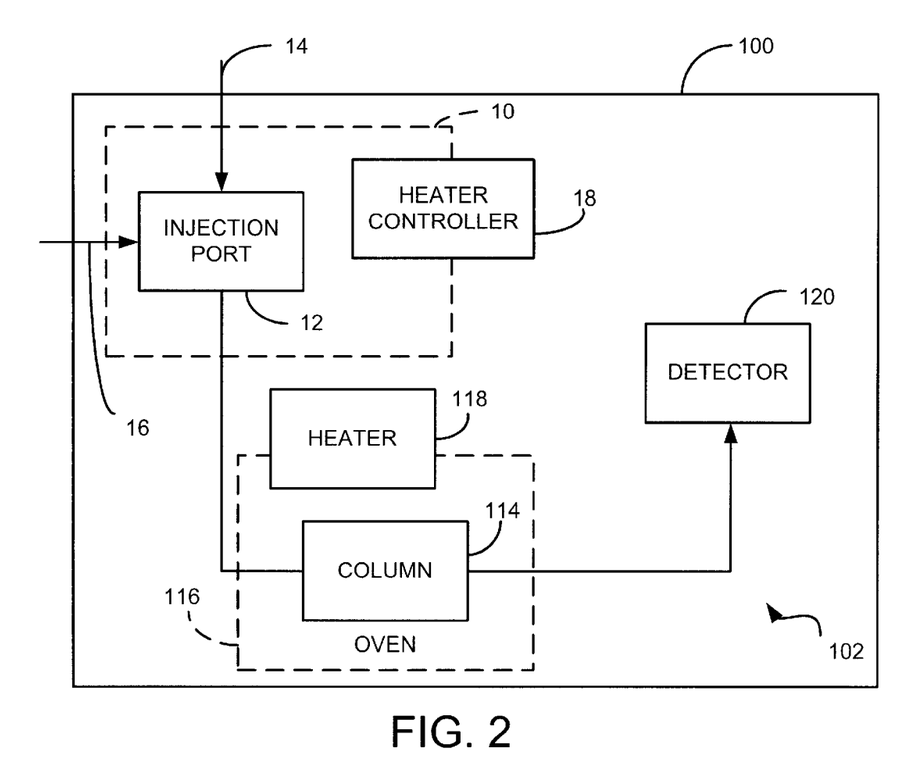
FIG. 2 is a schematic diagram of a preferred embodiment of the present invention.

As shown in greater detail in FIG. 2, analytical instrument system 100 and, more specifically, sample introduction apparatus 10 preferably incorporates an injection port 12 which is adapted to receive a sample, represented by arrow 14, and a flow of carrier gas, represented by arrow 16. Additionally, sample introduction apparatus 10 may incorporate electrical power and control circuitry (heater controller) 18 for heating the sample to a desired temperature.

In order to perform a chromatographic separation of a sample, a quantity of the sample typically is injected into the flow of carrier gas, preferably provided in the form of a pressurized stream. The sample introduction apparatus 10 then provides at least a portion of the sample/carrier gas mixture to a separation column 114. Preferably, column 114 is positioned within a chamber or oven 116 which is temperature controlled by one or more heaters and control circuitry 118. In order to ensure that the temperature within the oven 116 is maintained at a desired level, temperatures produced by the heater and control circuitry 118 (as well as 18) may be controlled with signals generated by the gas chromatographic apparatus 102 (FIG. 1). Thus, the sample/carrier gas mixture provided to the column 114 may be exposed to a controlled temperature profile.

As the sample/carrier gas mixture exits separation column 114, the presence of one or more analytes may be detected by detector 120. Typically, a detector output signal may be provided to computing apparatus 104 (FIG. 1), and optionally stored in the storage apparatus 110. Preferably, the detector output signal is provided in the form of data representative of a series of sample peaks in at least one sample peak series. The sample peaks may then by identified and presented in one or more sample peak series. Each sample peak series is analyzed with the aid of a peak identification method based on data representative of one or more selected standard peak groups. Preferably, data representative of the standard peak group has been predetermined or input at the input/output 108 and stored in the storage apparatus 110.

Figure 3:
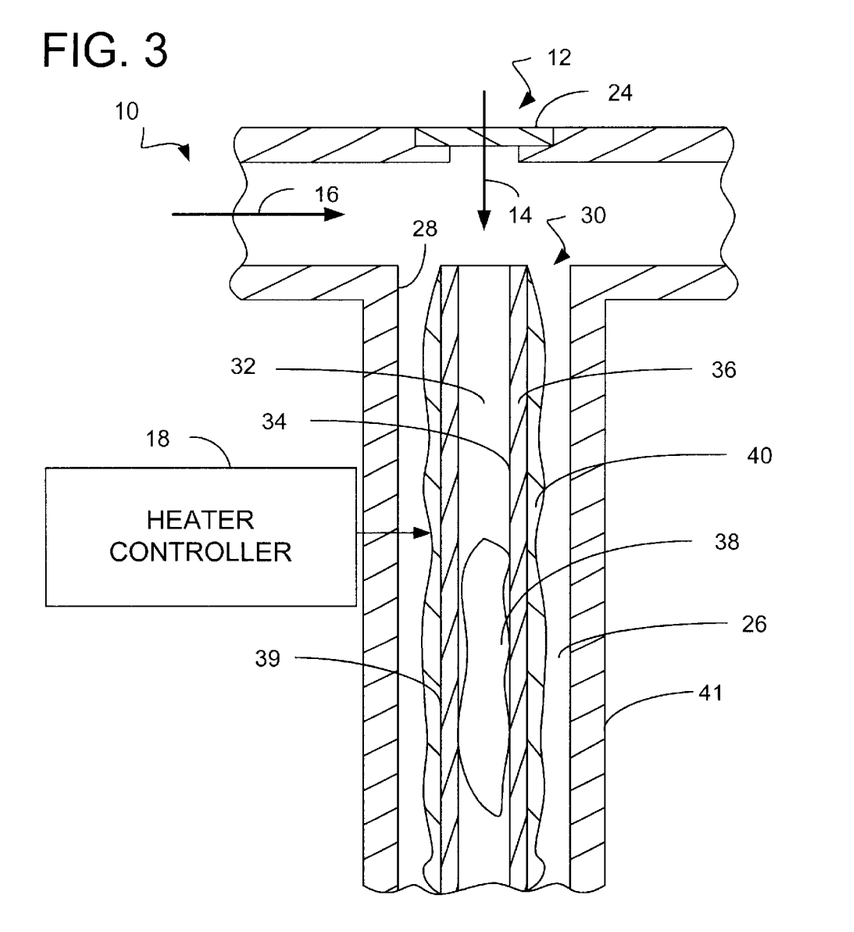
FIG. 3 is a partially cut-away, cross-sectional view of a preferred embodiment of a sample introduction apparatus of the present invention.
Figure 4:
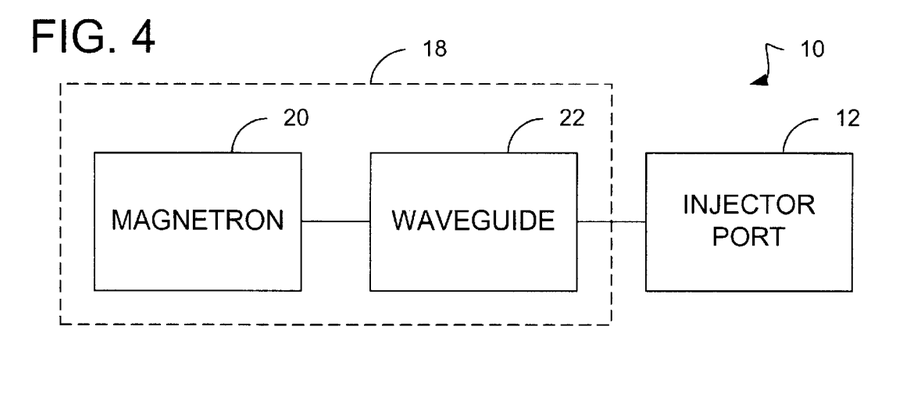
FIG. 4 is a partially cut-away, cross-sectional view of an alternative embodiment of a sample introduction apparatus of the present invention.

Referring now to FIGS. 3 and 4, a preferred embodiment of a sample introduction apparatus 10 of the present invention will now be described in detail. As shown in FIG. 3, injection port 12 may incorporate a septum 24, which provides a physical barrier for preventing contaminates from entering the injection port. Septum 24, however, is adapted for injecting sample 14 therethrough, such as by use of a syringe, for example, so that the sample may be mixed with carrier gas 16 within a channel 26 (defined, at least in part, by wall 28) of the sample introduction apparatus 10 to form a sample/carrier mixture.

As depicted in FIG. 3, the sample/carrier mixture is provided to a sample inlet liner 30. Liner 30, which preferably is formed of glass or fused silica, for example, incorporates a channel 32, which is defined by an interior surface 34 of liner wall 36, and also may incorporate a matrix 38 disposed within channel 32, which is provided to form a controlled array of interstices and pathways that are sufficient to provide a tortuous path for the sample so that the matrix temporarily retains the sample within the liner. Additionally, the exterior surface 39 of liner 30 preferably incorporates a coating 40, i.e., a semi-conductive coating, which may be formed of various materials, such as tin oxide, tin oxide with various metal additives, or tin salts, for example. It should be noted that coating 40 may be provided on various surfaces of the sample introduction apparatus, in addition to or to the exclusion of exterior surface 39, including, but not limited to, interior surface 34, interior surface 28, and exterior surface 41, among others.

For those embodiments incorporating a coating on the exterior surface of the sample inlet liner, a preferred method for applying the semi-conductive coating to the sample inlet liner utilizes a dip-coating process, although various other conventional methods may be utilized. As is known in such a dip-coating process, the semi-conductive coating, i.e., tin oxide, for instance, is prepared to a desired concentration by mixing tin oxide solids, for example, in an appropriate solvent to form a dipping slurry. The sample inlet liner then is dipped, partially dried, and then redipped in the slurry until a coating of desired distribution and thickness is achieved. The dipped sample inlet then is baked resulting in a sample inlet liner which is coated with a semi-conductive coating possessing desired resistive characteristics.

As depicted in FIG. 4, a preferred embodiment of the sample introduction apparatus 10 may incorporate microwave energy source 18, which includes a magnetron 20 for producing electromagnetic energy in the form of microwaves, and a wave-guide 22 coupling the magnetron to the semiconductively-coated sample inlet liner. Waveguide 22 is provided in a vicinity of at least a portion of the coating 40 so that microwave energy provided from the magnetron 20 may be directed toward the coating, thereby heating the coating. So configured, heat from the coating is transferred through the liner wall to the sample contained within the sample inlet liner.

Figure 5:
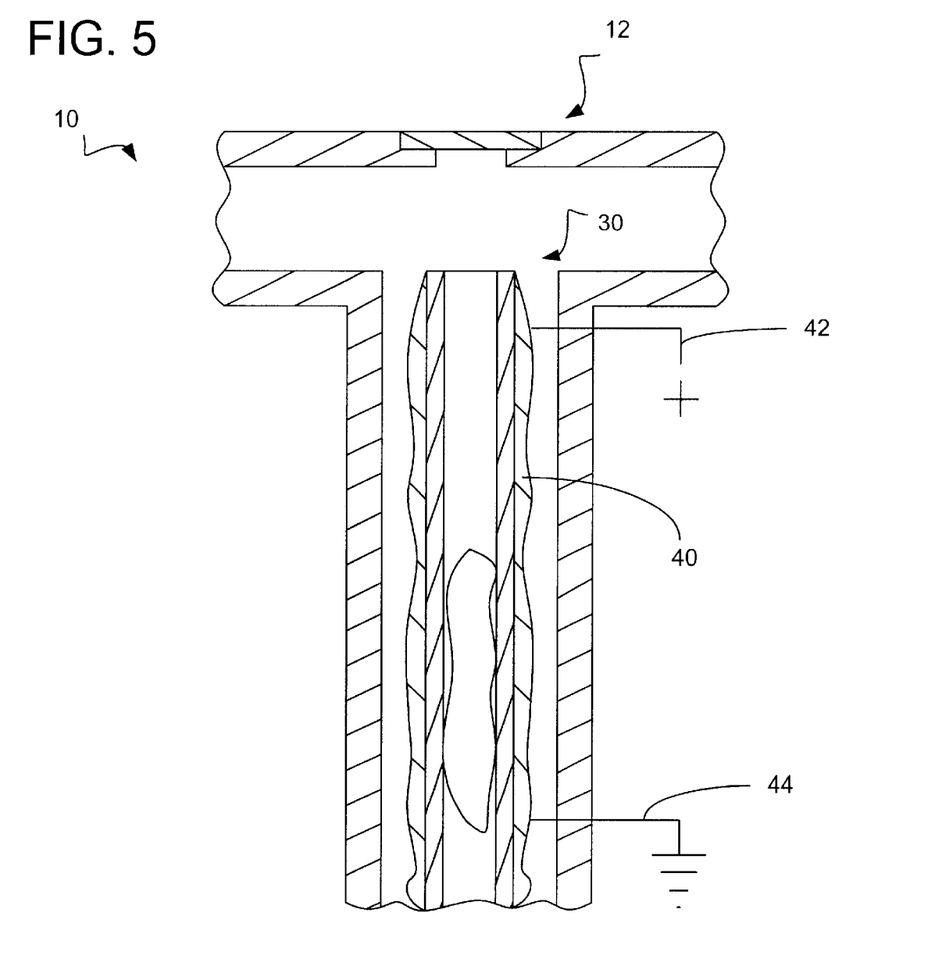
FIG. 5 is a partially cut-away, cross-sectional view of an alternative embodiment of a sample introduction apparatus of the present invention.

Referring now to the alternative embodiment depicted in FIG. 5, electrical connections, such as connections 42 and 44, may be provided at a spaced interval along the length of the liner 30, versus the magnetron and wave-guide combination depicted in FIG. 4. So provided, an electrical potential may be applied across the connections, thereby heating the coating. For example, during testing of a prototype apparatus of the configuration depicted in FIG. 5, a 40 volt dc potential was applied across a 40 ohm resistance coating, which was applied to a conventional fused silica sample inlet liner. Temperature ramp rates in excess of 600° C. per minute were recorded in open air.

As mentioned briefly hereinbefore, a traditional prior art inlet heater commonly incorporates a block of material, such as aluminum or stainless steel in which a cartridge heater and a temperature sensor is installed and, oftentimes, requires the use of a large power supply. Typically, such a heater and its associated heater block weighs approximately 4 oz. Since the inlet mass of such a heater can be approximately 2/32 Slugs (2 pounds weight), the heater typically must be configured from 60 watts to achieve reasonable heat-up rates and to maintain 300° C. to 400° C. steady state temperatures.

In contrast, preferred embodiments of the conductively coated heaters of the present invention weight approximately 1/100 oz. as they typically only need to heat the glass or fused silica liner mass, which typically is less than 1 oz. As a result heating rates can be orders of magnitude faster, using less power, and the steady state power required to maintain temperature settings is reduced to only few watts. So provided, such a heater provides for potentially large gains in temperature ramp rate and substantially reduced power requirements in order to maintain an elevated temperature using 400 times less mass.

Figure 6:
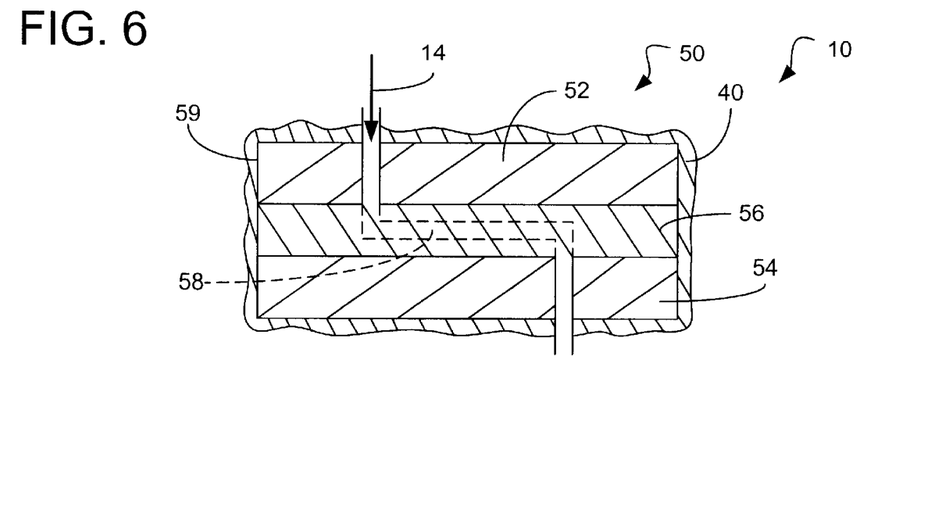
FIG. 6 is a partially cut-away, cross-sectional view of an alternative embodiment of a sample introduction apparatus of the present invention.

As depicted in the alternative embodiment of FIG. 6, the coating 40 also may be applied to a sample introduction apparatus that is configured as a micro-injector. A representative micro-injector 50 typically includes first and second layers of glass, 52 and 54 respectively, with a silicon die 56 disposed therebetween. Typically, the silicon die may be etched with one or more channels 58, which are adapted to receive a sample 14. Similar to the embodiments depicted in FIGS. 4 and 5, micro-injector 50, which is particularly well suited for use in a micro gas chromatograph, may be adapted for use with either a magnetron wave-guide combination or electrical connections (described hereinbefore) for heating the coating 40. As depicted in FIG. 6, the coating preferably is applied, at least in part, to an exterior surface 59 of the micro-injector.

Figure 7:
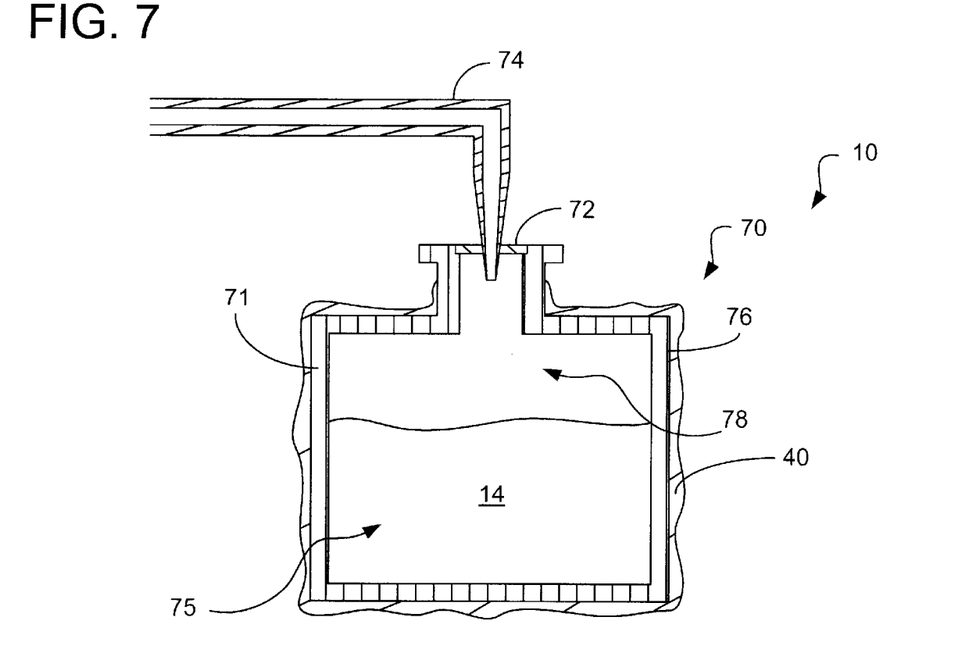
FIG. 7 is a partially cut-away, cross-sectional view of a preferred embodiment of a sample introduction apparatus of the present invention.

As depicted in FIG. 7, an alternative embodiment of the present invention may be configured for use in a head-space type sample introduction apparatus. As depicted therein, such a sample introduction apparatus typically incorporates the use of a vial 70, which contains an amount of sample 14 primarily in liquid phase. Typically, vial 70 includes a wall 71 and is provided with a septum 72, which is adapted to be penetrated by a portion of a sample transfer device, such as transfer line 74. The sample transfer device is adapted to fluidly communicate with a channel (or interior) 75 of the vial and to provide an amount of gaseous phase sample from the vial to a chromatographic apparatus. In some embodiments, coating 40 is applied to an exterior surface 76 of the vial 70 and may be heated, as described hereinbefore, so that at least a portion of the liquid phase sample is transformed to gaseous phase at the upper portion or headspace 78 of the vial, thereby allowing gaseous phase sample to enter the transfer line 74.

Figure 8:
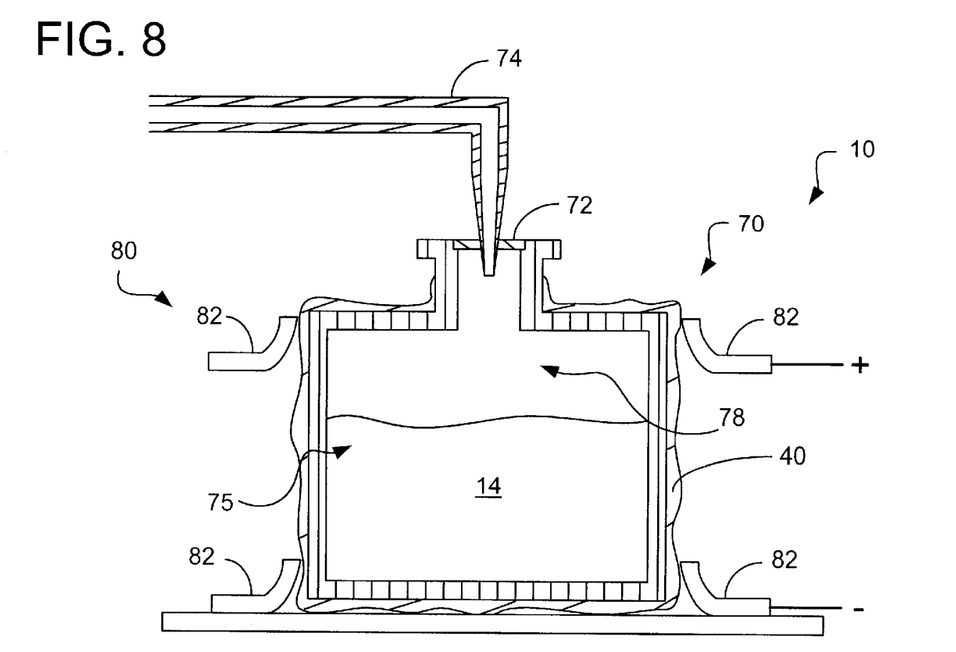
FIG. 8 is a partially cut-away, cross-sectional view of the embodiment depicted in FIG. 7 showing detail of a preferred vial mounting arrangement.

As depicted in the embodiment of FIG. 8, a vial mount 80 is provided for securing the position of the vial as well as for facilitating the delivery of electrical energy to the coating of the vial. Preferably, both of the aforementioned functions are facilitated by the use of spring fingers 82. Spring fingers 82, which may be formed of beryllium copper, or other suitable materials, cooperate with each other to firmly grasp the exterior of the vial 70 and provide suitable transmission paths for electricity to be delivered from the heater controller and to the coating.

Figure 9:
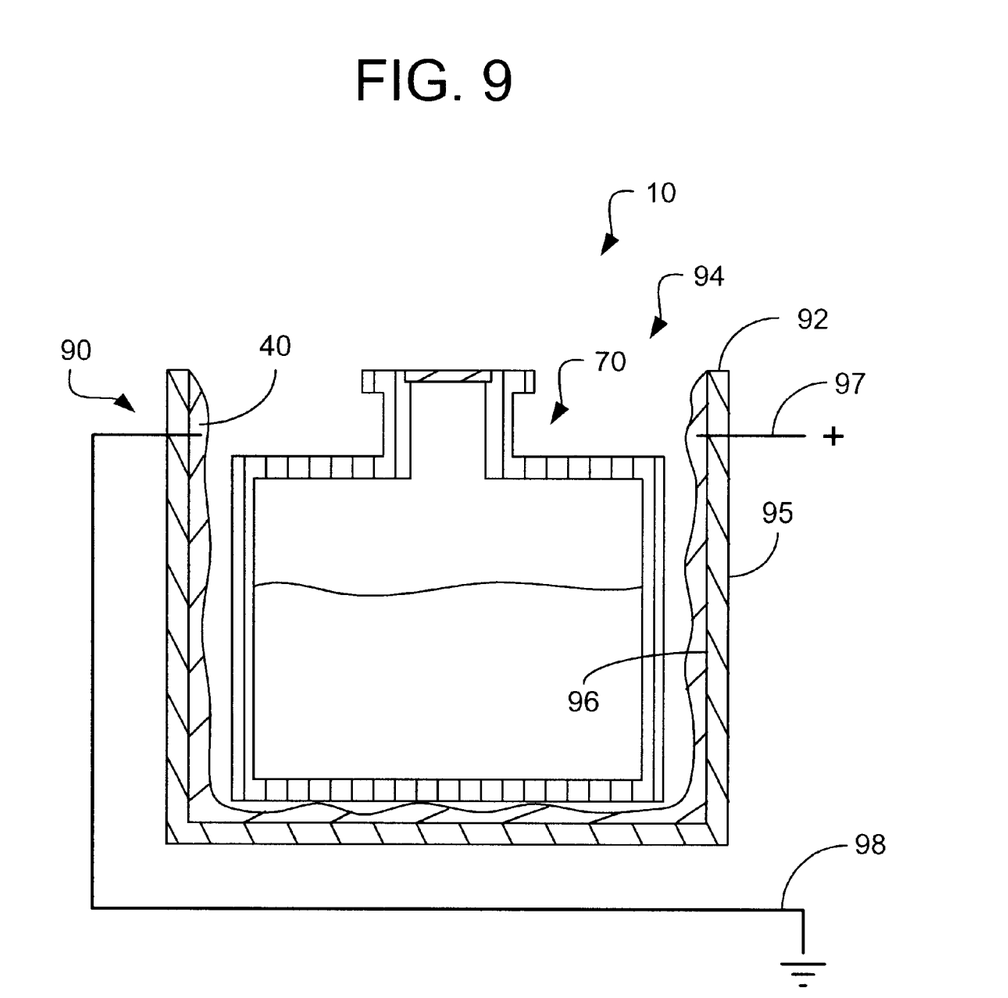
FIG. 9 is a partially cut-away, cross-sectional view of a preferred embodiment of a sample introduction apparatus of the present invention.

As depicted in FIG. 9, an alternative embodiment of the head-space sample introduction apparatus is depicted. In this embodiment, a vial mount 90 (defined, at least in part, by wall 92) is provided which is adapted to receive vial 70 within a channel 94 thereof. Preferably, one or more surfaces, i.e., exterior surface 95 and/or interior surface 96, of the vial mount are provided with a coating 40, with the coating being adapted for heating (as described hereinbefore) such as through the use of leads 97 and 98, or by a magnetron-waveguide assembly (not shown). So configured, coatings 40 need not be applied to each vial 70.

The foregoing description has been presented for purposes of illustration and description. It is not intended to be exhaustive or to limit the invention to the precise forms disclosed. Obvious modifications or variations are possible in light of the above teachings. The embodiment or embodiments discussed, however, were chosen and described to provide the best illustration of the principles of the invention and its practical application to thereby enable one of ordinary skill in the art to utilize the invention in various embodiments and with various modifications as are suited to the particular use contemplated. All such modifications and variations, are within the scope of the invention as determined by the appended claims when interpreted in accordance with the breadth to which they are fairly and legally entitled.

What is claimed is:

1. A sample introduction apparatus for use in providing a sample to a chromatographic apparatus, the chromatographic apparatus having a separation column and a heater, the separation column being adapted to receive a mixture of a carrier gas and at least a portion of the sample, the heater being adapted to heat the mixture received within the separation column, said sample introduction apparatus comprising:

a first wall defining a first channel, said first channel being configured to receive a sample to be provided to a chromatographic apparatus and being adapted to engage in fluid communication with the separation column of the chromatographic apparatus;

a coating of semi-conductive material arranged adjacent to at least a portion of said first wall; and a heater controller electro-magnetically communicating with said coating and configured to increase a temperature of said coating such that said coating, in response to receiving electro-magnetic energy from said heater controller, increases in temperature, thereby increasing a temperature of the sample, wherein said heater controller comprises a magnetron and waveguide, said magnetron and said waveguide being configured to generate microwaves and to provide said microwaves to said coating such that the temperature of the sample increases.

2. A sample introduction apparatus for use in providing a sample to a chromatographic apparatus, the chromatographic apparatus having a separation column and a heater, the separation column being adapted to receive a mixture of a carrier gas and at least a portion of the sample, the heater being adapted to heat the mixture received within the separation column, said sample introduction apparatus comprising:

a first wall defining a first channel, said first channel being configured to receive a sample to be provided to a chromatographic apparatus and being adapted to engage in fluid communication with the separation column of the chromatographic apparatus;

a coating of semi-conductive material arranged adjacent to at least a portion of said first wall; and a heater controller electro-magnetically communicating with said coating and configured to increase a temperature of said coating such that said coating, in response to receiving electro-magnetic energy from said heater controller, increases in temperature, thereby increasing a temperature of the sample, wherein said coating engages an interior surface of said first wall.

3. A sample introduction apparatus for use in providing a sample to a chromatographic apparatus, the chromatographic apparatus having a separation column and a heater, the separation column being adapted to receive a mixture of a carrier gas and at least a portion of the sample, the heater being adapted to heat the mixture received within the separation column, said sample introduction apparatus comprising:

a first wall defining a first channel, said first channel being configured to receive a sample to be provided to a chromatographic apparatus and being adapted to engage in fluid communication with the separation column of the chromatographic apparatus;

a coating of semi-conductive material arranged adjacent to at least a portion of said first wall; and a heater controller electro-magnetically communicating with said coating and configured to increase a temperature of said coating such that said coating, in response to receiving electro-magnetic energy from said heater controller, increases in temperature, thereby increasing a temperature of the sample, wherein said coating is comprised of tin oxide.

4. A sample introduction apparatus for use in providing a sample to a chromatographic apparatus, the chromatographic apparatus having a separation column and a heater, the separation column being adapted to receive a mixture of a carrier gas and at least a portion of the sample, the heater being adapted to heat the mixture received within the separation column, said sample introduction apparatus comprising:

a first wall defining a first channel, said first channel being configured to receive a sample to be provided to a chromatographic apparatus and being adapted to engage in fluid communication with the separation column of the chromatographic apparatus;

a coating of semi-conductive material arranged adjacent to at least a portion of said first wall; and a heater controller electro-magnetically communicating with said coating and configured to increase a temperature of said coating such that said coating, in response to receiving electro-magnetic energy from said heater controller, increases in temperature, thereby increasing a temperature of the sample, wherein said coating is comprised of at least one of the group consisting of tin salts.

5. A sample introduction apparatus for use in providing a sample to a chromatographic apparatus, the chromatographic apparatus having a separation column and a heater, the separation column being adapted to receive a mixture of a carrier gas and at least a portion of the sample, the heater being adapted to heat the mixture received within the separation column, said sample introduction apparatus comprising:

a first wall defining a first channel, said first channel being configured to receive a sample to be provided to a chromatographic apparatus and being adapted to engage in fluid communication with the separation column of the chromatographic apparatus;

a coating of semi-conductive material arranged adjacent to at least a portion of said first wall; and a heater controller electro-magnetically communicating with said coating and configured to increase a temperature of said coating such that said coating, in response to receiving electro-magnetic energy from said heater controller, increases in temperature, thereby increasing a temperature of the sample, wherein said first channel is adapted to receive a sample inlet liner therein, said sample inlet liner having an exterior surface and an interior surface, said interior surface defining a liner channel, said liner channel being configured to receive the sample to be provided to a chromatographic apparatus and being adapted to engage in fluid communication with the separation column of the chromatographic apparatus, and wherein said coating is applied to at least a portion of said exterior surface of said sample inlet liner.

6. The sample introduction apparatus of claim 2, wherein said heater controller has a first electrical trace and a second electrical trace, said first electrical trace and said second electrical trace being spaced from each other and each being engaged in electrical communication with said coating, said heater controller being configured to apply an electrical potential across said first electrical trace and said second electrical trace such that the temperature of the sample increases.

7. A sample introduction apparatus for use in providing a sample to a chromatographic apparatus, the chromatographic apparatus having a separation column and a heater, the separation column being adapted to receive a mixture of a carrier gas and at least a portion of the sample, the heater being adapted to heat the mixture received within the separation column, said sample introduction apparatus comprising:

a first wall defining a first channel, said first channel being configured to receive a sample to be provided to a chromatographic apparatus and being adapted to engage in fluid communication with the separation column of the chromatographic apparatus;

a coating of semi-conductive material arranged adjacent to at least a portion of said first wall; and a heater controller electro-magnetically communicating with said coating and configured to increase a temperature of said coating such that said coating, in response to receiving electro-magnetic energy from said heater controller, increases in temperature, thereby increasing a temperature of the sample, wherein said first wall defines a vial configured to retain the sample therein, and wherein said coating engages an exterior surface of said vial.

8. A sample introduction apparatus for use in providing a sample to a chromatographic apparatus, the chromatographic apparatus having a separation column and a heater, the separation column being adapted to receive a mixture of a carrier gas and at least a portion of the sample, the heater being adapted to heat the mixture received within the separation column, said sample introduction apparatus comprising:

a first wall defining a first channel, said first channel being configured to receive a sample to be provided to a chromatographic apparatus and being adapted to engage in fluid communication with the separation column of the chromatographic apparatus;

a coating of semi-conductive material arranged adjacent to at least a portion of said first wall; and a heater controller electro-magnetically communicating with said coating and configured to increase a temperature of said coating such that said coating, in response to receiving electro-magnetic energy from said heater controller, increases in temperature, thereby increasing a temperature of the sample, wherein said first wall defines a vial configured to retain the sample therein, said wherein said sample introduction apparatus has a vial mount having a second wall defining a second channel, said second channel being configured to receive at least a portion of said vial therein, said coating engaging an interior surface of said second wall.

9. A chromatographic analytical instrument system for analyzing a sample comprising:

a separation column adapted to receive a mixture of a carrier gas and at least a portion of a sample; and a sample introduction apparatus having a wall, a coating and a heater controller, said wall defining a channel, said channel being configured to receive the sample and being adapted to engage in fluid communication with said separation column, said coating being formed at least partially of a semi-conductive material and being arranged adjacent to at least a portion of said wall, said heater controller being arranged in a heat-transfer relationship with at least a portion of said coating and being configured to provide energy to said coating such that a temperature of said coating increases, thereby causing a temperature of the sample to increase, wherein said heater controller comprises a magnetron and waveguide, said magnetron and said waveguide being configured to generate microwaves and to provide said microwaves to said coating such that the temperature of the sample increases.

10. A chromatographic analytical system for analyzing a sample comprising:

a separation column adapted to receive a mixture of a carrier gas and at least a portion of a sample; and a sample introduction apparatus having a wall, a coating and a heater controller, said wall defining a channel, said channel being configured to receive the sample and being adapted to engage in fluid communication with said separation column, said coating being formed at least partially of a semi-conductive material and being arranged adjacent to at least a portion of said wall, said heater controller being arranged in a heat-transfer relationship with at least a portion of said coating and being configured to provide energy to said coating such that a temperature of said coating increases, thereby causing a temperature of the sample to increase, wherein said coating is comprised of tin oxide.

11. A method for providing a sample to a chromatographic apparatus, the chromatographic apparatus having a separation column and a heater, the separation column being adapted to receive a mixture of a carrier gas and at least a portion of the sample, the heater being adapted to heat the mixture received within the separation column, said method comprising the steps of:

providing a channel configured to receive a sample to be provided to a chromatographic apparatus, the channel being adapted to engage in fluid communication with the separation column of the chromatographic apparatus, the channel having a coating of semi-conductive material arranged adjacent to at least a portion thereof;

providing a sample inlet liner having an exterior surface and an interior surface, the sample inlet liner being configured to be received within the channel, the interior surface defining a liner channel, the liner channel being configured to receive the sample to be provided to a chromatographic apparatus and being adapted to engage in fluid communication with the separation column of the chromatographic apparatus, the coating being applied to at least a portion of the exterior surface of the sample inlet liner;

heating the coating such that a temperature of the sample increases within the channel; and providing the sample to the separation column of the chromatographic apparatus.

12. A method for providing a sample to a chromatographic apparatus, the chromatographic apparatus having a separation column and a heater, the separation column being adapted to receive a mixture of a carrier gas and at least a portion of the sample, the heater being adapted to heat the mixture received within the separation column, said method comprising the steps of:

providing a channel configured to receive a sample to be provided to a chromatographic apparatus, the channel being adapted to engage in fluid communication with the separation column of the chromatographic apparatus, the channel having a coating of semi-conductive material arranged adjacent to at least a portion thereof;

providing a vial, the vial defining the channel and being adapted to contain the sample to be provided to the chromatographic apparatus, the vial having the coating of semi-conductive material applied thereto;

heating the coating such that a temperature of the sample increases within the channel; and providing the sample to the separation column of the chromatographic apparatus.

13. A method for providing a sample to a chromatographic apparatus, the chromatographic apparatus having a separation column and a heater, the separation column being adapted to receive a mixture of a carrier gas and at least a portion of the sample, the heater being adapted to heat the mixture received within the separation column, said method comprising the steps of:

providing a channel configured to receive a sample to be provided to a chromatographic apparatus, the channel being adapted to engage in fluid communication with the separation column of the chromatographic apparatus, the channel having a coating of semi-conductive material arranged adjacent to at least a portion thereof;

providing a vial, the vial defining the channel and being adapted to contain the sample to be provided to the chromatographic apparatus; and providing a wall having the coating of semi-conductive material applied thereto, the wall being arranged in a heat-transfer relationship with the vial;

heating the coating such that a temperature of the sample increases within the channel; and providing the sample to the separation column of the chromatographic apparatus.

14. A method for providing a sample to a chromatographic apparatus, the chromatographic apparatus having a separation column and a heater, the separation column being adapted to receive a mixture of a carrier gas and at least a portion of the sample, the heater being adapted to heat the mixture received within the separation column, said method comprising the steps of:

providing a channel configured to receive a sample to be provided to a chromatographic apparatus, the channel being adapted to engage in fluid communication with the separation column of the chromatographic apparatus, the channel having a coating of semi-conductive material arranged adjacent to at least a portion thereof;

providing a magnetron and waveguide, the magnetron and the waveguide being configured to generate microwaves;

delivering microwaves to the coating such that the temperature of the coating increases, thereby increasing the temperature of the sample;

heating the coating such that a temperature of the sample increases within the channel; and providing the sample to the separation column of the chromatographic apparatus.

15. A method for providing a sample to a chromatographic apparatus, the chromatographic apparatus having a separation column and a heater, the separation column being adapted to receive a mixture of a carrier gas and at least a portion of the sample, the heater being adapted to heat the mixture received within the separation column, said method comprising the steps of:

providing a channel configured to receive a sample to be provided to a chromatographic apparatus, the channel being adapted to engage in fluid communication with the separation column of the chromatographic apparatus, the channel having a coating of semi-conductive material arranged adjacent to at least a portion thereof;

providing a first electrical trace and a second electrical trace spaced from each other and each being engaged in electrical communication with the coating; and applying an electrical potential across the first electrical trace and the second electrical trace such that the temperature of the coating increases, thereby increasing the temperature of the sample;

heating the coating such that a temperature of the sample increases within the channel; and providing the sample to the separation column of the chromatographic apparatus.

16. The sample introduction apparatus of claim 1, wherein said coating engages an interior surface of said first wall.

17. The sample introduction apparatus of claim 3, wherein said coating engages an interior surface of said first wall.

18. The sample introduction apparatus of claim 4, wherein said coating engages an interior surface of said first wall.

19. The sample introduction apparatus of claim 9, wherein said coating engages an interior surface of said first wall.

20. The sample introduction apparatus of claim 10, wherein said coating engages an interior surface of said first wall.

21. The sample introduction apparatus of claim 7, wherein said coating engages an interior surface of said first wall.

22. The sample introduction apparatus of claim 1, wherein said coating is comprised of tin oxide.

23. The sample introduction apparatus of claim 16, wherein said coating is comprised of tin oxide.

24. The sample introduction apparatus of claim 9, wherein said coating is comprised of tin oxide.

25. The sample introduction apparatus of claim 5, wherein said coating is comprised of tin oxide.

26. The sample introduction apparatus of claim 7, wherein said coating is comprised of tin oxide.

27. The sample introduction apparatus of claim 8, wherein said coating is comprised of tin oxide.

28. The sample introduction apparatus of claim 1, wherein said coating is comprised of at least one of the group consisting of tin salts.

29. The sample introduction apparatus of claim 16, wherein said coating is comprised of at least one of the group consisting of tin salts.

30. The sample introduction apparatus of claim 9, wherein said coating is comprised of at least one of the group consisting of tin salts.

31. The sample introduction apparatus of claim 5, wherein said coating is comprised of at least one of the group consisting of tin salts.

32. The sample introduction apparatus of claim 7, wherein said coating is comprised of at least one of the group consisting of tin salts.

33. The sample introduction apparatus of claim 8, wherein said coating is comprised of at least one of the group consisting of tin salts.

34. The sample introduction apparatus of claim 1, wherein said first channel is adapted to receive a sample inlet liner therein, said sample inlet liner having an exterior surface and an interior surface, said interior surface defining a liner channel, said liner channel being configured to receive the sample to be provided to a chromatographic apparatus and being adapted to engage in fluid communication with the separation column of the chromatographic apparatus, and wherein said coating is applied to at least a portion of said exterior surface of said sample inlet liner.

35. The sample introduction apparatus of claim 2, wherein said first channel is adapted to receive a sample inlet liner therein, said sample inlet liner having an exterior surface and an interior surface, said interior surface defining a liner channel, said liner channel being configured to receive the sample to be provided to a chromatographic apparatus and being adapted to engage in fluid communication with the separation column of the chromatographic apparatus.

36. The sample introduction apparatus of claim 23, wherein said first channel is adapted to receive a sample inlet liner therein, said sample inlet liner having an exterior surface and an interior surface, said interior surface defining a liner channel, said liner channel being configured to receive the sample to be provided to a chromatographic apparatus and being adapted to engage in fluid communication with the separation column of the chromatographic apparatus, and wherein said coating is applied to at least a portion of said exterior surface of said sample inlet liner.

37. The sample introduction apparatus of claim 4, wherein said first channel is adapted to receive a sample inlet liner therein, said sample inlet liner having an exterior surface and an interior surface, said interior surface defining a liner channel, said liner channel being configured to receive the sample to be provided to a chromatographic apparatus and being adapted to engage in fluid communication with the separation column of the chromatographic apparatus, and wherein said coating is applied to at least a portion of said exterior surface of said sample inlet liner.

38. The sample introduction apparatus of claim 2, further comprising:
    means for applying an electric potential across said coating.

39. The sample introduction apparatus of claim 3, wherein said heater controller has a first electrical trace and a second electrical trace, said first electrical trace and said second electrical trace being spaced from each other and each being engaged in electrical communication with said coating, said heater controller being configured to apply an electrical potential across said first electrical trace and said second electrical trace such that the temperature of the sample increases.

40. The sample introduction apparatus of claim 4, wherein said heater controller has a first electrical trace and a second electrical trace, said first electrical trace and said second electrical trace being spaced from each other and each being engaged in electrical communication with said coating, said heater controller being configured to apply an electrical potential across said first electrical trace and said second electrical trace such that the temperature of the sample increases.

41. The sample introduction apparatus of claim 5, wherein said heater controller has a first electrical trace and a second electrical trace, said first electrical trace and said second electrical trace being spaced from each other and each being engaged in electrical communication with said coating, said heater controller being configured to apply an electrical potential across said first electrical trace and said second electrical trace such that the temperature of the sample increases.

42. The sample introduction apparatus of claim 7, wherein said heater controller has a first electrical trace and a second electrical trace, said first electrical trace and said second electrical trace being spaced from each other and each being engaged in electrical communication with said coating, said heater controller being configured to apply an electrical potential across said first electrical trace and said second electrical trace such that the temperature of the sample increases.

43. The sample introduction apparatus of claim 8, wherein said heater controller has a first electrical trace and a second electrical trace, said first electrical trace and said second electrical trace being spaced from each other and each being engaged in electrical communication with said coating, said heater controller being configured to apply an electrical potential across said first electrical trace and said second electrical trace such that the temperature of the sample increases.

44. The sample introduction apparatus of claim 1, wherein said first wall defines a vial configured to retain the sample therein, and wherein said coating engages an exterior surface of said vial.

45. The sample introduction apparatus of claim 36, wherein said first wall defines a vial configured to retain the sample therein.

46. The sample introduction apparatus of claim 4, wherein said first wall defines a vial configured to retain the sample therein, and wherein said coating engages an exterior surface of said vial.

47. The sample introduction apparatus of claim 1, wherein said first wall defines a vial configured to retain the sample therein, said wherein said sample introduction apparatus has a vial mount having a second wall defining a second channel, said second channel being configured to receive at least a portion of said vial therein, said coating engaging an interior surface of said second wall.

48. The sample introduction apparatus of claim 47, wherein said first wall defines a vial configured to retain the sample therein, said wherein said sample introduction apparatus has a vial mount having a second wall defining a second channel, said second channel being configured to receive at least a portion of said vial therein, said vial mount having a second coating engaging an interior surface of said second wall.

49. The sample introduction apparatus of claim 7, wherein said first wall defines a vial configured to retain the sample therein, said wherein said sample introduction apparatus has a vial mount having a second wall defining a second channel, said second channel being configured to receive at least a portion of said vial therein, said vial mount having a coating engaging an interior surface of said second wall.

50. The chromotographic analytical instrument system of claim 10, wherein said heater controller comprises a magnetron and waveguide, said magnetron and said waveguide being configured to generate microwaves and to provide said microwaves to said coating such that the temperature of the sample increases.

51. The method of claim 11, wherein the step of heating the coating comprises the steps of:
    providing a magnetron and waveguide, the magnetron and the waveguide being configured to generate microwaves;
    delivering microwaves to the coating such that the temperature of the coating increases, thereby increasing the temperature of the sample.

52. The method of claim 12, wherein the step of heating the coating comprises the steps of:
    providing a magnetron and waveguide, the magnetron and the waveguide being configured to generate microwaves;
    delivering microwaves to the coating such that the temperature of the coating increases, thereby increasing the temperature of the sample.

53. The method of claim 13, wherein the step of heating the coating comprises the steps of:
    providing a magnetron and waveguide, the magnetron and the waveguide being configured to generate microwaves;
    delivering microwaves to the coating such that the temperature of the coating increases, thereby increasing the temperature of the sample.

* * * * *